(12) United States Patent
Nair et al.

(10) Patent No.: US 8,632,815 B2
(45) Date of Patent: Jan. 21, 2014

(54) PROCESS FOR NANOEMULSIFICATION OF CURCUMIN AND DERIVATIVES OF CURCUMIN

(75) Inventors: Anitha Krishnan Nair, Chennai (IN); Ramchand Nanappan Chaniyilparampu, Chennai (IN); Kiran Bhupathiraju, Vijayawada (IN); Rama Raju Gokaraju, Vijayawada (IN); Ganga Raju Gokaraju, Vijayawada (IN); Trimurtulu Golakoti, Vijayawada (IN)

(73) Assignee: Laila Pharmaceutical Pvt., Ltd., Chennai (IN)

( * ) Notice: Subject to any disclaimer, the term of this patent is extended or adjusted under 35 U.S.C. 154(b) by 0 days.

(21) Appl. No.: 13/129,424

(22) PCT Filed: Nov. 17, 2009

(86) PCT No.: PCT/IN2009/000651
§ 371 (c)(1),
(2), (4) Date: May 16, 2011

(87) PCT Pub. No.: WO2010/070665
PCT Pub. Date: Jun. 24, 2010

(65) Prior Publication Data
US 2011/0229532 A1    Sep. 22, 2011

(30) Foreign Application Priority Data

Nov. 17, 2008  (IN) ............................ 2828/CHE/2008

(51) Int. Cl.
*A61K 9/14* (2006.01)
*A61K 9/51* (2006.01)

(52) U.S. Cl.
CPC . *A61K 9/14* (2013.01); *A61K 9/145* (2013.01); *A61K 9/51* (2013.01); *A61K 9/5123* (2013.01); *A23V 2250/2112* (2013.01); *Y10S 977/773* (2013.01); *Y10S 977/915* (2013.01)
USPC ........... 424/489; 424/400; 514/649; 977/773; 977/915; 977/773

(58) Field of Classification Search
None
See application file for complete search history.

(56) References Cited

U.S. PATENT DOCUMENTS

| 4,263,333 A | * | 4/1981 | Maing et al. ................ 426/540 |
| 2003/0236236 A1 | | 12/2003 | Chen et al. |
| 2006/0067998 A1 | | 3/2006 | Kurzrock et al. |

FOREIGN PATENT DOCUMENTS

| WO | WO 2007043058 A1 | * | 4/2007 |
| WO | 2010010431 A | | 1/2010 |
| WO | WO 2010070665 A3 | * | 10/2010 |

OTHER PUBLICATIONS

X Wang, Y Jiang, YW Wang, MT Huang, CT Ho, Q Huang. "Enhancing anti-inflammation activity of curcumin through O/W nanoemulsions." Food Chemistry, vol. 108, 2008, pp. 419-424, published Nov. 17, 2007.*
S Baboota, F Shakeel, A Ahuja, J Ali, S Shafiq. "Design, development and evaluation of novel nanoemulsion formulations for transdermal potential of celecoxib." Acta Pharm, vol. 57, 2007, pp. 315-332.*
TG Mason, JN Wilking, K Meleson, CB Chang, SM Graves. "Nanoemulsions: formation, structure, and physical properties." Journal of PHysics: Condensed Matter, vol. 18, 2006, pp. R635-R666.*
S Bisht, G Feldmann, S Soni, R Ravi, C Karikar, A Maitra, A Maitra. "Polymeric nanoparticle-encapsulated curcumin ("nanocurcumin"): a novel strategy for human cancer therapy." Journal of Nanobiotechnology, vol. 5:3, 2007, pp. 1-18, Published Apr. 17, 2007.*
J Ishida, H Ohtsu, Y Tachibana, Y Nakanishi, KF Bastow, M Nagai, HK Wang, H Itokawa, KH Lee. "Antitumor Agents. Part 214: Synthesis and Evaluation of Curcumin Analogues as Cytotoxic Agents." Bioorganic & Medicinal Chemistry, vol. 10, 2002, pp. 3481-3487.*
Wang et al., "Enhancing anti-inflammation activity of curcumin through O/W nanoemulsions" Food Chemistry, vol. 108, No. 2: p. 419-424, Nov. 17, 2007.

* cited by examiner

*Primary Examiner* — Frederick Krass
*Assistant Examiner* — Isaac Shomer
(74) *Attorney, Agent, or Firm* — Kramer Amado, P.C.

(57) ABSTRACT

A process for nanomulsification of highly lipophillic polyphenols compounds using non-ionic surfactant and a non-ionic co-solvent with the help of sonar energy, to enhance the aqueous solubility is disclosed herein.

20 Claims, 5 Drawing Sheets

PROCESS FOR NANOEMULSIFICATION OF CURCUMIN AND DERIVATIVES OF CURCUMIN

FIELD OF THE INVENTION

The present invention relates to a novel process for nanoemulsification of the highly lipophillic polyphenolic compounds such as curcuminoids using non-ionic surfactants and a non-ionic cosolvent at a particular concentration together with the help of sonar energy, to enhance the aqueous solubility.

BACKGROUND OF INVENTION

Curcuminoids are curcumins and derivatives of curcumins with different chemical groups. These compounds are polyphenols and produce yellow color. The characteristics of many curcuminoid compounds are unsuitable for drug design since they have poor solubility in water at acidic and physiological pH, and also hydrolyze rapidly in alkaline solutions. Therefore, curcumin derivatives are synthesized to increase their solubility and hence bioavailability (*Studies on curcumin and curcuminoids XXXI. Symmetric and asymmetric curcuminoids: Stability, activity and complexation with cyclodextrin*. Author(s): Tomren M A (Tomren, M A.), Masson M (Masson, M), Loftsson T (Loftsson, T.), Tonnesen H H (Tonnesen, H. Hjorth). Source: *INTERNATIONAL JOURNAL OF PHARMACEUTICS* 338 (1-2): 27-34 Jun. 29, 2007). Curcuminoids are soluble in dimethyl sulfoxide (DMSO), acetone and ethanol (*Formulation and characterization of curcuminoids loaded solid lipid nanoparticles*. Author(s): Tiyaboonchai W (Tiyaboonchai, Waree), Tunpradit W (Tunpradit, Watcharaphorn), Plianbangchang P (Plianbangchang, Pinyupa). Source: *INTERNATIONAL JOURNAL OF PHARMACEUTICS* 337 (1-2): 299-306 Jun. 7, 2007 but are poorly soluble in lipids. It's possible to increase their solubility in aqueous phase with surfactants or co-surfactants (*Antioxidant activities of curcumin, demethoxycurcumin and bis-demethoxycurcumin*. Author(s): Jayaprakasha G K, Rao L I, Sakariah K K Source: *FOOD CHEMISTRY* 98 (4): 720-724 2006): There have been synthesized curcumin derivatives that could possible be more potent than curcumin. Most common derivatives have different substituents on the phenyl groups (*Formulation and characterization of curcuminoids loaded solid lipid nanoparticles*. Author(s): Tiyaboonchai W (Tiyaboonchai, Waree), Tunpradit W (Tunpradit, Watcharaphorn), Plianbangchang P (Plianbangchang, Pinyupa). Source: *INTERNATIONAL JOURNAL OF PHARMACEUTICS* 337 (1-2): 299-306 Jun. 7, 2007. Now there is an increasing demand for demethoxycurcumin and (curcuminoids) because of their recently discovered biological activity (*Antioxidant activities of curcumin, demethoxycurcumin and bis-demethoxycurcumin*. Author(s): Jayaprakasha G K, Rao L I, Sakariah K K Source: *FOOD CHEMISTRY* 98 (4):720-724 2006).

Natural curcuminoids are those extracted from the *Curcuma longa* plant and they are majorly comprised of 3 constituents a). Curcumin b) demethoxycurcumin c) bis-demethoxycurcumin. Several studies have shown that their pharmacological effects are comparable to those of corticosteroids and non-steroidal anti inflammatory drugs.

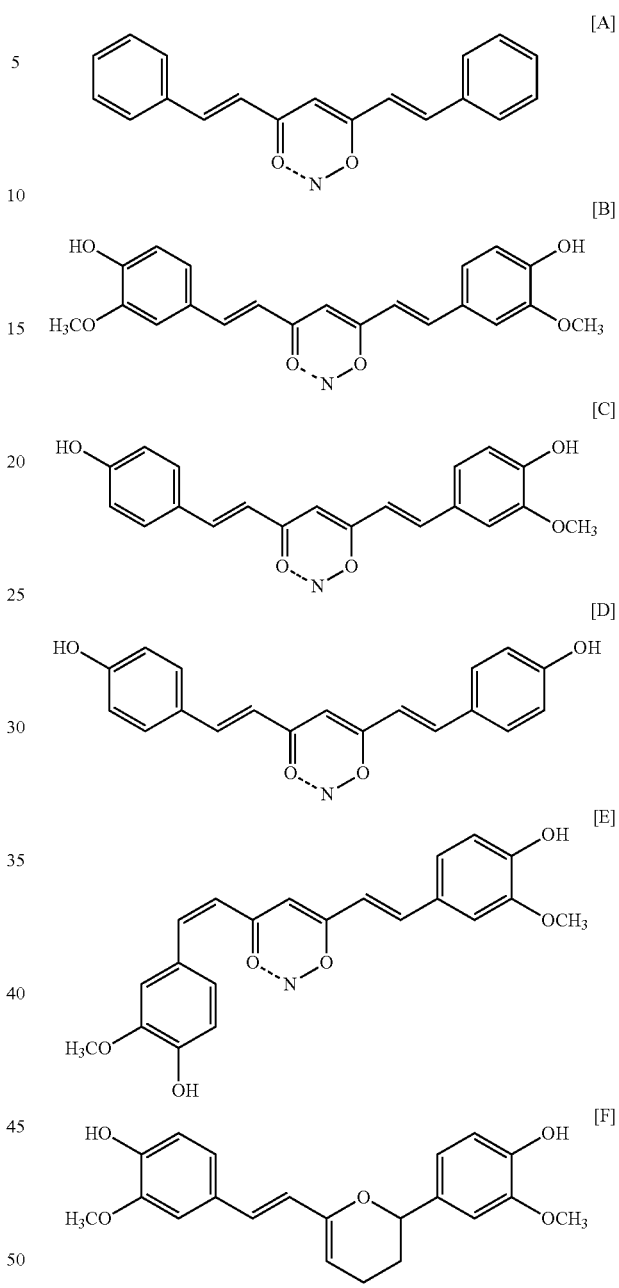

FIG. 1

Curcumin (FIG. 1B) was isolated in 1815 and structurally defined in 1910. Other curcuminoids isolated from *Curcuma longa* include demethoxycurcumin (FIG. 1 C), bis-demethoxycurcumin (FIG. 1 D), a cis-trans geometrical isomer of curcumin (FIG. 1 E), and cyclocurcumin (FIG. 1 F)

Thus, in the view of its structure it is evident that the solubility of curcuminoids is very poor in aqueous solutions. Thus quite a number of studies are in progress with regard to increasing its solubility in water and the prior art relevant in this regard is listed below:

PCT/US2007/005829 describes Curcuminoid formulations having enhanced bioavailability are provided and comprise a curcuminoid, antioxidant, glucuronidation inhibitor, and water-soluble, pharmaceutically acceptable inhibitor. A method of treating Alzheimer's and other age-related diseases by administering such a composition is also provided and also a method to solubilize curcuminoids through nanoemulsions.

PCT/KR2004/000529 describes a method for solubilization of curcumin and dispersion into water. The method prepares a water-soluble curcumin by covalent-bonding of sugar with the curcumin, thereby making the curcumin, which was insoluble in water, into a water-soluble curcumin.

Biji T Kurien et al have described yet another process to solubilize curcumin through the use of heat energy. (*Improving the Solubility and Pharmacological Efficacy of Curcumin by Heat Treatment—ASSAY and Drug Development Technologies*, Aug. 1, 2007, 5(4): 567-576. doi:10.1089/adt.2007.064)

BISHT et al have encapsulated the curcumin particles using nanoencapsulation terming it 'nanocurcumin'. *Polymeric nanoparticle-encapsulated curcumin ("nanocurcumin"): a novel strategy for human cancer therapy Journal of Nanobiotechnology* Apr. 17, 2007, 5:3

TOMREN M A *Studies on curcumin and curcuminoids XXXI. Symmetric and asymmetric curcuminoids: Stability, activity and complexation with cyclodextrin.* Author(s): Tomren M A (Tomren, M A.), Masson M (Masson, M), Loftsson T (Loftsson, T.), Tonnesen H H (Tonnesen, H. Hjorth). Source: *INTERNATIONAL JOURNAL OF PHARMACEUTICS* 338 (1-2): 27-34 Jun. 29, 2007)

It is a well known fact that curcumin has very low bioavailability as it undergoes metabolism very rapidly and results in excretion of 98% of the curcumin. With only 2% of the compound absorbed by the body, it still brings about remarkable efficacy in the treatment of lot of diseases.

Although, the use of non-ionic surfactants has been discussed for solubilization purpose in the above mentioned literatures, they appear to be in a different context. The surfactants used have been done so in order to make emulsions and the likes and not for directly solubilizing curcuminoids.

Therefore, the current invention aims to enhance the aqueous solubility of the highly lipophillic polyphenolic compounds such as curcuminoids using non-ionic surfactants and a non-ionic cosolvent at a specific concentration together with the help of sonar energy.

OBJECTIVE OF THE INVENTION

The main objective of the current invention is to solubilize highly lipophilic polyphenolic compounds like curcuminoids (natural and synthetically derived) in an ampiphillic medium thereby rendering enhanced water solubility.

SUMMARY OF THE INVENTION

Figure 1:
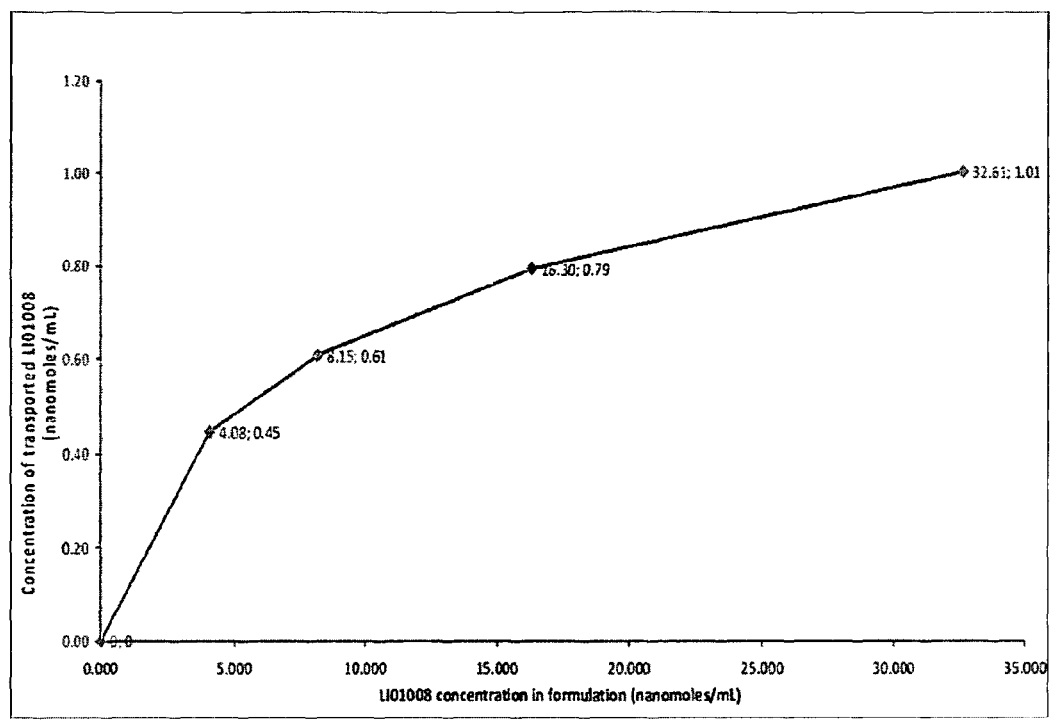
FIG. 1: The dose response curve indicating a concentration dependent increase in the transport of nanoemulsified LI01008 across A549 cell monolayers

The current invention discloses a novel process for nanoemulsification of the highly lipophillic polyphenolic compounds such as curcuminoids using non-ionic surfactants and a non-ionic cosolvent at a specific concentration together with the help of sonar energy, to enhance the aqueous solubility.

DETAILED DESCRIPTION OF THE INVENTION

The invention will now be described in detail in connection with certain preferred and optional embodiments, so that various aspects thereof may be more fully understood and appreciated.

As used herein the term 'surfactant' means surface active agent which works by lowering the surface tension of water and enabling solubility of lipophilic compounds.

As used herein the term 'co-solvent' in the present context means a solvent which synergistically enhances the solubility of the lipophillic compound of the present invention.

According to the present, invention, a process is provided to solubilize the lipophillic compounds such as curcuminoids using non-ionic surfactant and non-ionic cosolvent with the help of sonar energy.

The surfactants are amphiphilic, meaning they contain a hydrophobic tail and a hydrophilic head. Therefore, they are soluble in both hydrophobic mediums and water. They are of 2 types a) ionic b) nonionic. The current invention involves the use of nonionic surfactants of pharmaceutical purpose. The surfactants used can be selected from polysorbate 80 and 20, poloxamers, octoxynol and any pharmaceutically acceptable nonionic surfactant.

Also mentioned is a cosolvent in the solubilization process which enables enhanced solubility due to synergism. The cosolvent used in this regard is polyethylene glycol (PEG-400). PEG 6000 can also be used.

According to the inventive process, upon adding the surfactant and cosolvent to the curcuminoids, the mixture needs to be stirred well and then subjected to sonication or use of sound energy of 25 Khz for 15-30 min depending on the sample size to solubilize the curcuminoid. The curcuminoids upto 2.5% can be solubilized using the method of the present invention.

Sonication enables solubilization of the curcuminoid by breaking intermolecular interactions and non-covalent bonds thereby aiding enhanced water solubility. The interesting feature of curcuminoids is the conjugated diene system in its structure that imparts its therapeutic properties. The sonar energy is not powerful enough to break these covalent bonds and hence the therapeutic property of curcuminoids is left without damage.

The synergistic activity to solubilize curcuminoids could be because of the interaction of the curcuminoids with the hydrophobic pocket of the nonionic surfactants that is present as a long chain hydrophobic tail which enables further complexation with the cosolvent that confers a mild charge to the whole complex aided by the sound energy provided through sonication. This mild charge aids in enhanced solubility in aqueous systems.

In accordance with the present invention, the process for solubilizing curcuminoids comprising the following steps:

a) stirring a mixture of curcuminoid and non ionic surfactant polysorbate 80 in 1:10 ratio;

b) adding nonionic cosolvent, polyethylene glycol in a ratio of 1:10 with reference to curcumin with continued stirring in order to disperse the curcuminoid particles well in the medium;

c) subjecting the above mixture to sonication for 15-30 mins with sound energy or till the curcuminoids are fully solubilized or until there are no visible particles in the mixture; and d) dispersing the above mixture into the aqueous phase followed by stirring well to solubilize curcuminoids in water.

The compositions prepared by using the solubilized curcuminoids as per the above process has shown marked increase in the transport of curcumin and improved bioavailability. The formulation is made using a unique nanoemulsification process which helps the compound to become more hydrophilic without any structural change to the compound thereby aiding in better transport and absorption, which is confirmed by both in vitro and in vivo studies.

The advantage of the present invention is that the curcuminoids used for solubilization can be taken upto 2.5% which is on the higher side for any pharmaceutical formulation.

The ratio of curcuminoid and nonionic surfactant is in the range of 1:10. Similarly, the ratio of curcuminoid and nonionic cosolvent is in the range of 1:10.

Nonionic surfactants and nonionic co-solvents are present in the amount of 1% each in the solution.

Thus, it is evident that even a highly lipophilic molecule like curcuminoids can be solubilized effectively by using the process of present invention, which is simple and does not involve any complicated procedures.

Although the use of surfactants is well documented in solubilization of lipophilic compounds in a hydrophilic medium, its use in conjunction with a nonionic cosolvent followed by the use of sonar energy to solubilize the same has not been reported in the literature. Thus, this invention can be extended to solubilize other lipophilic therapeutic compounds where time consuming and complicated procedures are involved.

Thus, the current invention has three aspects which makes it indispensable in an industrial set up which are 1) economical 2) uncomplicated procedures 3) Lowered time consumption.

The following examples, which include preferred embodiments, will serve to illustrate the practice of this invention, it being understood that the particulars shown are by way of example and for purpose of illustrative discussion of preferred embodiments of the invention.

EXAMPLE 1

Process for Nanoemulsification of Curcumin 12 g of curcumin 98% taken into a glass beaker and added 212 g of Polysorbate-80 and 224 g of Polyethylene glycol 400 and sonicated the mixture for 30 mins at 25 KHz, until completely dissolved.

EXAMPLE 2

Process for Nanoemulsification of Bis-o-Diemethyl Curcumin 12 g of bis-o-diemethyl curcumin taken into a glass beaker and added 212 g of Polysorbate-80 and 224 g of Polyethylene glycol 400 and sonicated the mixture for 30 mins at 25 KHz, until completely dissolved.

EXAMPLE 3

| SR. NO. | INGREDIENTS | RM CODE | SPECIFICATION | LABEL CLAIM | QTY/BATCH |
|---|---|---|---|---|---|
| 1. | Hydroxy Propyl Methyl Cellulose | RH-04 | I.P | 0.1% w/v | 20.0 g |
| 2. | Borax | RB-03 | I.P. | — | 4.670 g |
| 3. | Benzalkonium chloride (50%) solution | RB-02 | I.P. | 0.02% w/v | 4.0 g |
| 4. | Edetate disodium | RE-01 | I.P. | — | 20.0 g |
| 5. | Sodium chloride | RS-02 | I.P. | — | 159.1 g |
| 6. | Polyethylene glycol-400 | RP-09 | I.P. | — | 224 g |
| 7. | Polysorbate-80 | RT-02 | I.P. | — | 212 g |
| 8. | Curcumin 98% | RC-07 | I.H.S | 0.04-0.05% w/v | 12.0 g |
| 9. | Purified Water qs | — | — | — | 20.0 L |

Procedure for Preparation of Ophthalmic Formulation:

Preparation of Solution A:

1. Weighing accurately 20 gm of Hydroxypropyl methylcellulose and adding the same to a vessel containing 2 L water (10% of batch size) which is heated to about 90° C. and kept over night.

2. Stirring the said solution on the next day until dispersed completely and making the volume to 6 L (30% of batch size) with purified water and stirring the same well to get homogenous dispersion.

3. Filtering the said solution through 2µ prefilter into the filling vessel. This solution is then autoclaved.

Preparation of Solution B:

1. Collecting 14 L purified water, freshly in the manufacturing vessel. Weighing accurately 4.67 g of Borax, add to the manufacturing vessel. Stirring until completely dissolved.

2. weighing accurately 4 ml of Benzalkonium chloride solution and adding to the manufacturing vessel and stirring until completely dissolved;

3. weighing accurately 20 g of Edetate disodium and adding to the manufacturing vessel along with stirring until completely dissolved; and 4. weighing accurately 159 g of Sodium chloride and adding it to the manufacturing vessel along with stirring until completely dissolved.

Preparation of Solution C:

1. Weighing accurately 12 g of Curcumin 98% and adding it to the glass beaker;

2. measuring accurately 212 g of Polysorbate-80 and adding to a glass beaker of suitable size;

3. measuring accurately 224 g of Polyethylene glycol 400 and adding it to the beaker; and 4. sonicating the mixture for 30 mins, until completely dissolved.

Preparation of Bulk Solution:

1. Adding 'Solution C' with 'Solution B' and stir well;

2. filtering the solution through 0.2µ filter into the autoclaved filling vessel containing 'Solution A'; and 3. checking the pH which should be between 5.8-6.4.

EXAMPLE 4

Particle Size Distribution Data for Nanoemulsified Curcumin 98% and BDMC

A Particle size distribution study conducted on the nanoemulsified formulation has further confirmed that the curcumin molecules exist as nano sized particles in the current formulation. This study proves that a curcumin molecule which is originally 374 nm in the unformulated form is emulsified into 8-11 nm sized particles through a unique process, which has been indicated for this enhanced transport and efficacy of curcumin through our formulation.

The study was conducted using Malvern particle size analyzer. The map of scattering intensity versus angle is the primary source of information used to calculate the particle size. The scattering of particles is accurately predicted by the Mie scattering model allowing accurate sizing across the widest possible dynamic range. During the laser diffraction measurement, particles are passed through a focused laser beam. These particles scatter light at an angle that is inversely proportional to their size. The angular intensity of the scattered light is then measured by a series of photosensitive detectors. The advantage of this study is that there is no sample preparation involved.

The study conducted on the particle size distribution of curcumin 98% and nanoemulsified BDMC and curcumin 98% clearly showed the particle sizes of the nanoemulsified BDMC and curcumin 98% was between 8-11 nm which is the ideal size of a nano-emulsified compound when compared to the particle size of unformulated curcumin 98% which was 373 nm. This is a clear indication that the process of nanoemulsification followed has effectively transformed the large sized particles to nanosized coated curcuminoid particles. Additional peaks can be observed which is contributed by the high molecular weight excipients used to prepare the formulation. The results obtained demonstrate that the current nanoemulsification process used in the study is simple and effective.

EXAMPLE 5

In Vivo Bioavailability Study Conducted on Nanoemulsified Bis-o-Demethylcurcumin (BDMC)

Bioavailability of the above formulation was studied on A549 cell line of human lung carcinoma fibroblast cell line. These are adherent cells with quick growth capabilities. The cells were cultured in DMEM media until they reached ~90% confluency after which they were split into 12-well plates. When the culture plates become ~90-100% confluent, they were used for the experiment. Normally, a seeding density of $10^5$ cells per well can give rise to ~90% confluent cultures in 3 days time.

The effect of concentration of nanoemulsified Bis-o-demethylcurcumin, in a dose dependant manner on the transport efficiency of the said compound through A549 epithelial cell line was studied.

| Bis-o-demethylcurcumin conc. (nano-moles/mL) | Bis-o-demethylcurcumin conc from std. graph (nano-moles/mL) |
|---|---|
| 4.076 | 0.448 |
| 8.152 | 0.609 |
| 16.304 | 0.795 |
| 32.609 | 1.006 |

A dose response using varying concentrations of the formulation of the present invention was conducted to study the effect of one of the pharmacokinetic parameter on the transport of Bis-o-demethylcurcumin into the A549 cells. The dose response curve indicated by the graph (FIG. 1) representing the study undertaken indicates that there is definitely a concentration dependent increase in the transport of nanoemulsified Bis-o-demethylcurcumin across A549 cell monolayers and hence, it can be inferred that concentration is definitely a key parameter in the transport of nanoemulsified Bis-o-demethylcurcumin.

The transport of the formulation prepared according to the process disclosed hereinabove, was further studied in vivo through the ocular tissue of rabbits into the vitreous fluid. The vitreous fluid so collected and analyzed using HPLC. The compound was transported in detectable amounts and estimated at different time intervals.

EXAMPLE 5

In Vivo Anti-Cataract Efficacy of Curcumin 98% Ophthalmic Formulation

An in vivo efficacy experiment on the anti-cataract effect of the formulation indicates that the compound is able to permeate through the ocular barriers and reach the retina and prevents the cataract formation in rats.

Study was conducted to determine the anti-cataract effect of curcumin 98% ophthalmic formulation to develop a safe and effective treatment for the prevention or delay the cataract. Animals were grouped into Group I (control), Group II (sodium selenite) and Group III (treatment).

On 10th day of postnatal period, curcumin 98% ophthalmic formulation was instilled topically to the eyes of group III animals only. Two hours later Sodium Selenite (25 µM/kg·bw of 5 ml/kg·bw) was injected subcutaneously to both group II and III animals, thereafter 5 µl of LP002-09 was instilled topically to the eyes of group III animals only. The curcumin 98% ophthalmic formulation was instilled daily thrice at an interval of 4 hours for a period of one week, whereas the group I and II animals were left undisturbed through out the dosing period. During instillation of the curcumin 98% the eyelids of the rat pups were opened gently and carefully and held approximately one minute to prevent overflowing of curcumin 98% ophthalmic formulation.

All animals were observed individually through out the observation period for any clinical signs and mortality. On the examination day i.e. when the pups first opened their eyes, the development of cataract was observed by the presence or absence of opacity by dilating the pupil with 0.8% tropicamide.

The cataract was scored on a scale of 0 to 4 according to procedure described by Muranov et al., (2004). Grade 0 was a normal clear lens, Grade 1 was a subcapsular opacity; Grade 2 was nuclear cataract, Grade 3 was strong nuclear cataract; Grade 4 was dense opacity involving entire lens and the results have been presented in below table 1

TABLE 1

| | | Cataract Type | | | | | | |
|---|---|---|---|---|---|---|---|---|
| Group No. | No. of Eyes | No Opacity<br>0 | Subcapsular opacity<br>1 | Nuclear cataract Score<br>2 | Strong Nuclear cataract<br>3 | Dense opacity involving entire lens<br>4 | Total Percentage of cataract | Grade (Mean ± S.D.) |
| I Control | 20 | 20 | 0 | 0 | 0 | 0 | 0 | 00.0 ± 00.0 |
| II Sodium Selenite Treated | 20 | 0 | 0 | 2 | 4 | 14 | 100 | 3.6 ± 0.68 |
| III LP002-09 treated | 20 | 11 | 5 | 2 | 2 | 0 | 45 | 0.75 ± 1.02* |

*Highly significant (P < 0.0001*) at 5% level, vs. Sodium Selenite treated

Results:

None of the animals exhibited clinical signs of toxicity and mortality throughout the experimental period. All the eyes of group I (control) animals were found to be clear. In group II animals in which Sodium Selenite was injected developed dense opacity type cataract in 70% of eyes, strong nuclear cataract in 20% eyes and nuclear cataract in 10% of eyes where as in Group III (treatment) animals no cataract was observed in 55% (11 eyes) of the eyes, strong nuclear cataract in 10% (2 eyes), nuclear cataract in 10% (2 eyes) and subcapsular opacity in 25% (5 eyes) of eyes.

Under these experimental conditions, thus it is concluded that the instillation of Curcumin 98% ophthalmic formulation into the eye of Wistar rat pups effectively reduces the effect of selenite-induced cataract. Hence, the experiments conclude that curcumin is transported better through the formulation of the present invention, thereby leading to enhanced bioavailability resulting in improved efficacy.

Figure 2:
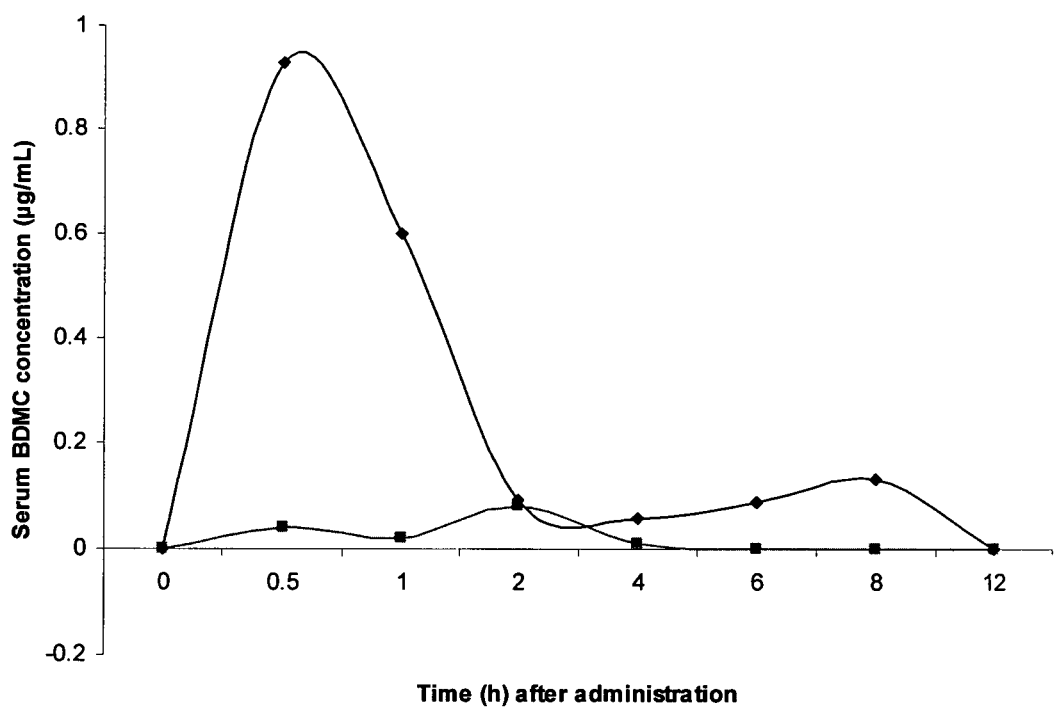
FIG. 2: Graph showing serum LI01008 (BDMC) concentration (ug/ml) over 12 hrs after administration.
Figure 3:
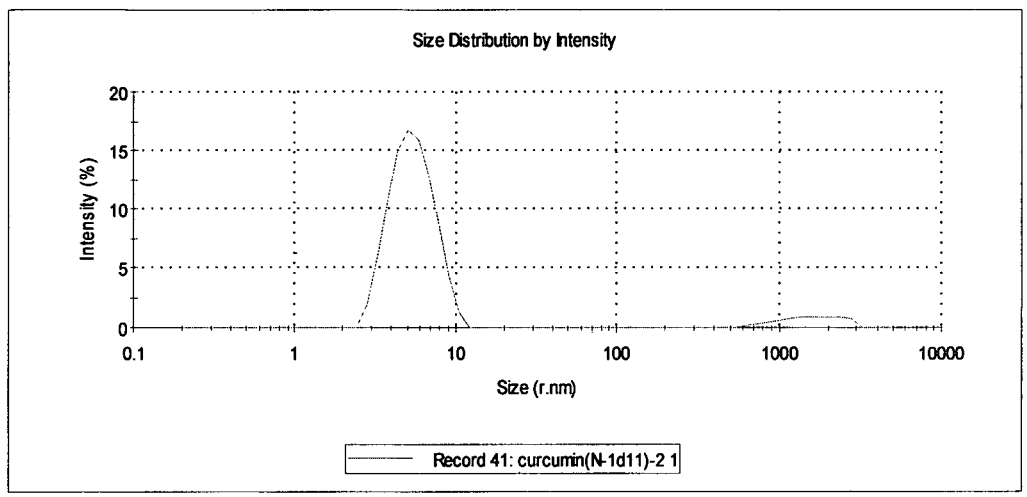
FIG. 3: The graph indicating the size of nano-emulsified curcumin 98%.
Figure 4:
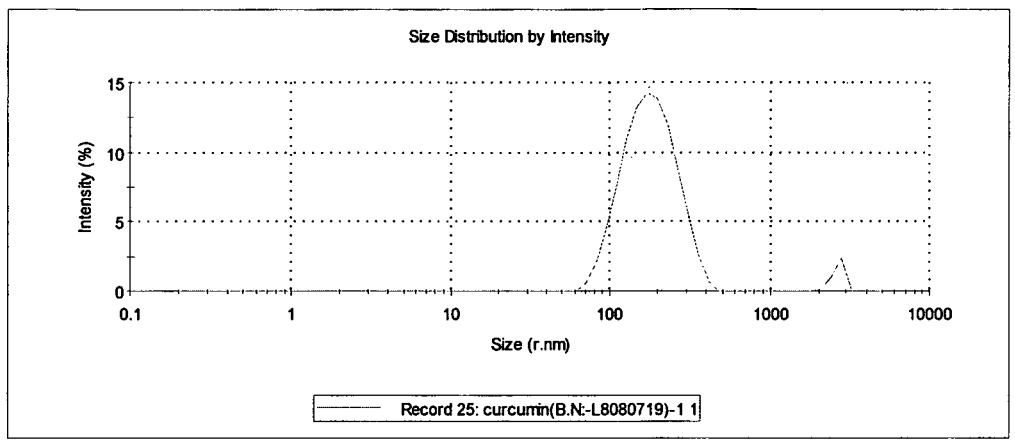
FIG. 4: The graph indicating the size of unformulated curcumin 98%.
Figure 5:
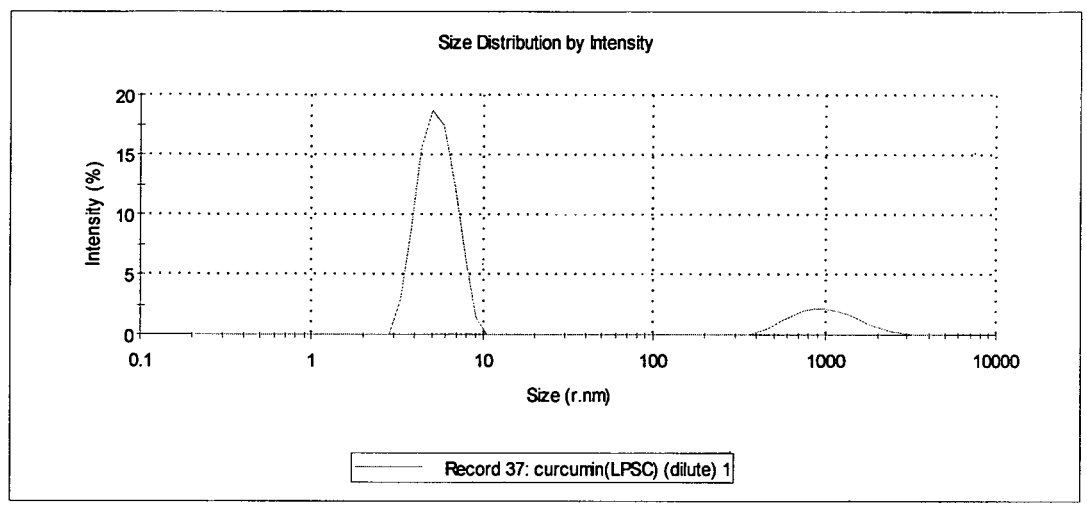
FIG. 5: The graph indicating the size of nano-emulsified BDMC.

In vivo oral bioavailability studies conducted on rats showed 14 times improved bioavailability, which is clearly depicted in the graph (FIG. 2) (graph given below, pink line-unformulated, blue line-formulated).

We claim:

1. A process for enhancing the aqueous solubility of a curcuminoid, comprising:
   a. sonicating said curcuminoid in a medium comprising a non-ionic surfactant and a non-ionic co-solvent, wherein said co-solvent is polyethylene glycol;
   wherein said sonicating produces nanoparticles of said curcuminoid having a log-normal particle size distribution with a peak particle size of between 1 nm and 50 nm.

2. The process as claimed in claim 1, wherein said curcuminoid is selected from the group consisting of natural curcuminoids, synthetically derived curcuminoids, and mixtures thereof.

3. The process as claimed in claim 2, wherein said natural curcuminoids are selected from the group consisting of curcumin, bisdemethoxycurcumin, demethoxycurcumin, and mixtures thereof.

4. The process as claimed in claim 2, wherein said synthetically derived curcuminoids are selected from the group consisting of demethylated curcuminoids.

5. The process as claimed in claim 1, wherein said surfactant is selected from the group consisting of polysorbate 80 and 20, poloxamers, and octoxynol.

6. The process as claimed in claim 1, wherein the ratio of curcuminoid to nonionic surfactant is from 1:10 to 1:18.

7. The process as claimed in claim 1, wherein the ratio of curcuminoid to nonionic co-solvent is from 1:10 to 1:19.

8. The process as claimed in claim 2, wherein said synthetically derived curcuminoids are bis-O-demethyl curcumin.

9. The process as claimed in claim 1, wherein said sonicating produces particles of said curcuminoid; and
   wherein said particles of said curcuminoid have a log-normal particle size distribution with a peak particle size of between 2 nm and 20 nm.

10. The process as claimed in claim 1, wherein said curcuminoid is present in an amount of 0.04% w/v to 2.5% w/v.

11. The process as claimed in claim 10, wherein said curcuminoid is selected from the group consisting of natural curcuminoids, synthetically derived curcuminoids, and mixtures thereof.

12. A process for enhancing the aqueous solubility of curcuminoids, comprising:
   a. nanoemulsifying said curcuminoids in a medium comprising a non-ionic surfactant and a non-ionic co-solvent with sonication, wherein said co-solvent comprises polyethylene glycol;
   wherein said nanoemulsifying produces nanoparticles of said curcuminoids having a log-normal particle size distribution with a peak particle size of between 2 nm and 20 nm.

13. A process to enhance the aqueous solubility of a curcuminoid, wherein said process comprises:
   a. stirring a mixture of the curcuminoid and a non-ionic surfactant to produce a mixture;
   b. adding polyethylene glycol to the mixture with continued stirring in order to disperse the curcuminoid in the mixture;
   c. subjecting the mixture to sonication to produce nanoparticles of the curcuminoid having a log-normal particle size distribution with a peak particle size of between 1 and 50 nm; and
   d. subsequent to subjecting the mixture to sonication, dispersing the mixture into an aqueous phase followed by stirring to solubilize the curcuminoids in water.

14. The process as claimed in claim 13, wherein said non-ionic surfactant is polysorbate 80, and said curcuminoid and said non-ionic surfactant are present in a ratio of from 1:10 to 1:18.

15. The process as claimed in claim 13, wherein said curcuminoid and polyethylene glycol are used in a ratio of from 1:10 to 1:19.

16. A process for enhancing the aqueous solubility of curcuminoids, comprising: nanoemulsifying said curcuminoids in a medium comprising a non-ionic surfactant and a non-ionic co-solvent with sonication to produce particles of said curcuminoids having a defined average particle size; wherein said defined average particle size is in the range of 8-11 nm.

17. A process for enhancing the aqueous solubility of curcuminoids, comprising:
   sonicating said curcuminoids in a medium comprising a non-ionic surfactant and a non-ionic co-solvent to produce a sonicated mixture containing nanoparticles of said curcuminoids;
   wherein said nanoparticles of said curcuminoids have a log-normal particle size distribution with a peak particle size of between 2 nm and 20 nm.

18. The process as claimed in claim 17, wherein the non-ionic co-solvent comprises polyethylene glycol.

19. The process as claimed in claim 17, further comprising dispersing the sonicated mixture in an aqueous phase.

20. A dispersion obtained by the process of claim 19.

* * * * *